United States Patent [19]
Takeya et al.

[11] Patent Number: 4,749,775
[45] Date of Patent: Jun. 7, 1988

[54] NOVEL POLYESTER POLYMERS

[75] Inventors: Tetsuro Takeya, Sodegaura; Tatsuya Tomioka, Kisarazu; Shigeru Murakami; Kenkichi Takahashi, both of Sodegaura, all of Japan

[73] Assignee: Idemitsu Kosan Co., Ltd., Tokyo, Japan

[21] Appl. No.: 70,553

[22] Filed: Jul. 7, 1987

[51] Int. Cl.$^4$ ............... C08G 69/44; C08G 73/16; C07D 209/02
[52] U.S. Cl. ............... 528/289; 525/444; 525/448; 528/171; 528/173; 528/184; 528/188; 528/194; 528/288; 528/292; 528/302; 528/305; 528/322; 548/455
[58] Field of Search ............... 525/444, 448; 528/171–173, 184, 188, 194, 288, 289, 292, 302, 305, 322; 548/455

[56] References Cited
U.S. PATENT DOCUMENTS

| | | | |
|---|---|---|---|
| 4,145,351 | 3/1979 | Schmidt et al. | 548/455 X |
| 4,146,702 | 3/1979 | Morris et al. | 528/191 |
| 4,265,802 | 5/1981 | Choe | 528/194 X |
| 4,412,058 | 10/1983 | Siemionko | 528/191 |
| 4,556,705 | 12/1985 | McCready | 528/289 |
| 4,599,397 | 7/1986 | Yoshimura et al. | 528/190 |

*Primary Examiner*—Lucille M. Phynes
*Attorney, Agent, or Firm*—Antonelli, Terry & Wands

[57] ABSTRACT

Polyester polymers consisting essentially of repeating units having the formula

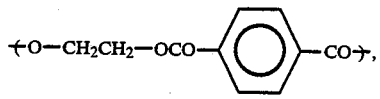

repeating units having the formula

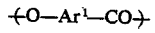

[II], repeating units having the formula

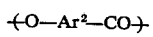

[III], and repeating units having the formula

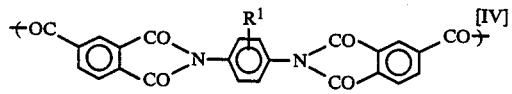

wherein
Ar$^1$ is selected from

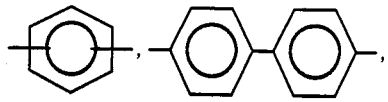

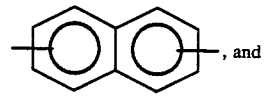

, and

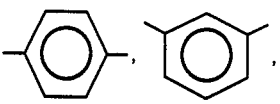

,

Ar$^2$ is selected from

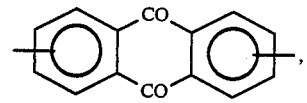

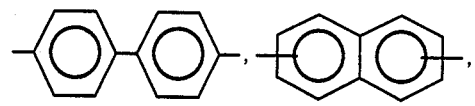

, halogen substituted radicals of these radicals, and

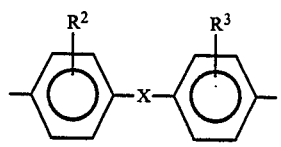

wherein
X is selected from —O—, —S—, —SO$_2$—, —CO—, —O(CH$_2$)$_n$O—, —CH$_2$)$_n$, and

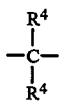

wherein each n independently represents a member having a value of from 1 to 10, and each R$^4$ is independently selected from alkyl radicals of 1 to 5 carbon atoms, and R$^2$ and R$^3$ are independently selected from hydrogen atom, halogen radicals, alkyl radicals of 1 to 5 carbon atoms, and phenyl radical, and R$^2$ and R$^3$ may be identical or different from each other, and R$^1$ is selected from halogen radicals and alkyl radicals of 1 to 5 carbon atoms, and wherein the polyester polymer has a reduced viscosity [$\eta$sp/c] of at least 0.2 dl/g as measured in p-chlorophenol at a concentration of 0.2 g/dl at 60° C.

Such polyester polymers are excellent in the mechanical strength and heat resistance and, therefore, are useful as various kinds of fibers; films or engineering plastics. A process for preparing the polyester polymer and novel diimide-dicarboxylic acid to be used as a material in this process are also disclosed.

16 Claims, No Drawings

NOVEL POLYESTER POLYMERS

BACKGROUND OF THE INVENTION

(1) Field of the Invention

The present invention relates to a novel polyester polymer which may be used as the raw material for electrical or electronic equipments, parts of machines, fibers, or the like, a process for preparing the same, and a novel diimide-dicarboxylic acid which is a raw material for preparing the polyester polymer. More particularly, the present invention relates to a novel polyester polymer excellent in the mechanical strength and heat resistance, which therefore is useful as various kinds of fibers, films, or engineering plastics.

(2) Description of the Prior Art

In orders to improve the properties of polyethyleneterephthalates, there is proposed in Japanese Laid-open Patent No. 72393/1974 a method of reacting a polyethyleneterephthalate with an acyloxy-aromatic carboxylic acid.

However, the modification by the reaction of the acyloxy-aromatic carboxylic acids has its limit in the improvement of the mechanical strength, and therefore, there is a demand for more excellent modified polyesters.

SUMMARY OF THE INVENTION

The object of the present invention is to solve such problems of the prior art and to provide novel polyester polymers and a process for preparing the same, which are improved in the mechanical strength by introducing novel constituting units into the above-mentioned polymers.

The inventors found, as the result of their diligent study to achieve the above-mentioned object, that an improved mechanical strength and heat resistance can be obtained by, in addition to an acyloxy aromatic carboxylic acid, further introducing other components into the polymeric chain, and the knowledge led them to complete the present invention.

Accordingly, the present invention provides a polyester polymer consisting essentially of repeating units having the formula

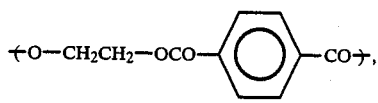   [I]

repeating units having the formula

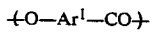   [II], repeating units having the formula

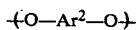   [III], and repeating units having the formula

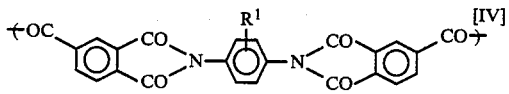   [IV]

wherein
Ar¹ is selected from

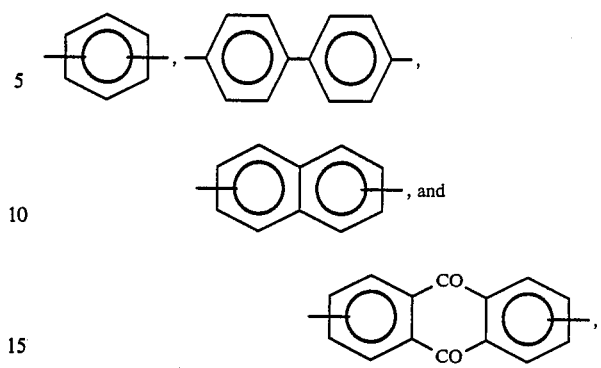

Ar² is selected from

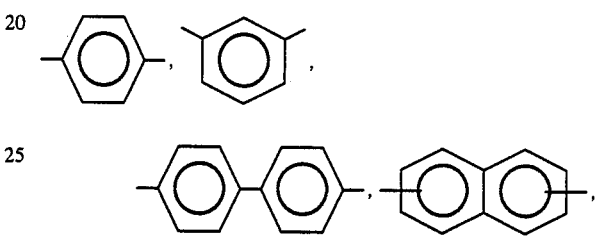

halogen substituted radicals of these radicals, and

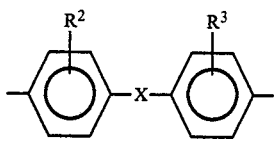

wherein
X is selected from —O—, —S—, —SO₂—, —CO—, —O(CH₂)ₙO—, —(CH₂)ₙ— and

wherein
each n is a number having a value of from 1 to 10, and
each R⁴ is independently selected from alkyl radicals of 1 to 5 carbon atoms, and
each R² and R³ is independently selected from hydrogen atom, halogen radicals, alkyl radicals of 1 to 5 carbon atoms, and phenyl radical, and
R¹ is selected from, halogen radicals, and alkyl radicals of 1 to 5 carbon atoms,
and wherein the polyester polymer has a reduced viscosity [ηsp/c] of at least 0.2 dl/g as measured in p-chlorophenol at a concentration of 0.2 g/dl at 60° C.

The novel polyester polymers of the present invention can be prepared by, for example, a process of the present invention which comprises reacting [A] a polyethyleneterephthalate, [B] an acyloxy-aromatic calboxylic acid, [C] an ester having the formula

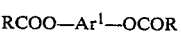

wherein each R is selected from alkyl radicals of 1 to 20 carbon atoms, and

Ar$^1$ is as defined above, and [D] a diimide-dicarboxylic acid having the formula

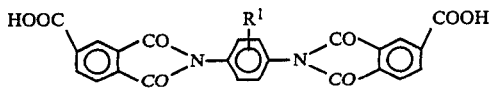

wherein R$^1$ is as defined above.

Another object of the present invention is to provide a novel diimide-dicarboxylic acid which is a main raw material of the polyester polymers of the present invention, that is, a diimide-dicarboxylic acid having the formula

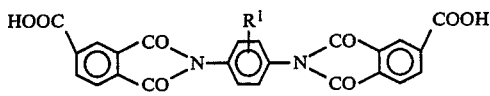

wherein R$^1$ is as defined above.

DETAILED DESCRIPTION OF THE INVENTION

The preferred polyester polymers of the present invention comprise 5 to 50% of the repeating units having the formula [I], 5 to 70% of the repeating units having the formula [II], 5 to 50% of the repeating units having the formula [III], and 5 to 50% of the repeating units having the formula [IV], in mole fraction. When the values of the mole fractions of [III] and [IV] are smaller than these ranges, the improvement of the strength is insufficient, and values larger than these ranges causes a decrease in the moldability. It is more preferable that the mole fractions of [III] and [IV] are identical.

If the reduced viscosity is less than 0.2 dl/g, sufficient mechanical strength cannot be obtained.

The polyethyleneterephthalates [A] to be used for preparing the polyester polymers of the present invention, which are not to be particularly limited, usually have a reduced viscosity [$\eta$sp/c] of from 0.1 to 1.0 dl/g as measured in p-chlorophenol at a concentration of 0.2 g/dl at 60° C. Further, polyethyleneterephthalates in which the dicarboxylic acid component and the diol component are modified to other components in a range where the object of the present invention is not missed may also be used.

The preferred acyloxy-aromatic carboxylic acids [B], which are not to be particularly limited, have the general formula R$^5$—CO—O—Ar$^1$—COOH wherein R$^5$ is selected from alkyl radicals of 1 to 3 carbon atoms and Ar$^1$ is as defined above.

The illustrative examples of the acyloxy-aromatic carboxylic acids include m-acetoxybenzoic acid, p-acetoxybenzoic acid, 4-acetoxy-3-methoxybenzoic acid, 4-acetoxy-3-chlorobenzoic acid, 4-acetoxy-3,5-dichlorobenzoic acid, 4-(4'-acetoxyphenyl)benzoic acid, 2-acetoxy-6-naphthoic acid, 2-acetoxy-7-naphthoic acid, and 2-acetoxy-7-anthraquinonecarboxylic acid. Among these, p-acetoxybenzoic acid and 4-(4'-acetoxyphenyl)benzoic acid are particularly preferable.

The illustrative examples of the esters [C] to be used in the present invention include 4,4'-diacetoxybiphenyl, p-phenylene diacetate, m-phenylene diacetate, naphthylene diacetate, bis(4-acetoxyphenyl)ether, bis(4-acetoxyphenyl)sulfide, bis(4-acetoxyphenyl)sulfone, bis(4-acetoxyphenyl)ketone, 2,2-bis(4-acetoxyphenyl)propane, 2,2-bis(3-methyl-4-acetoxyphenyl)propane, 1,2-bis(4-acetoxyphenyl)ethane, and halogen substituted derivatives of these.

The diimide-dicarboxylic acids to be used in the present invention are novel compounds and are useful as the raw materials of polyesterimides and the like since they have an improved melt-polymerization ability in comparison with known diimide-dicarboxylic acid. The preferred dicarboxylic acids [D] to be used include 1,4-bis(4'-carboxyphthalimido)-2-chlorobenzene, and 1,4-bis(4'-carboxyphthalimido)-2-methylbenzene. These compounds can be prepared by reacting trimellitic anhydride with a derivative of 1,4-diaminobenzene having the formula

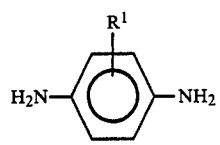

wherein R$^1$ is as defined above.

Although the above-mentioned derivatives of diaminobenzene are not to be particularly limited, 1,4-diamino-2-chlorobenzene and 1,4-diamino-2-methylbenzene dihydrochloride are preferably used from the view point of the availability of the raw materials.

The reaction is carried out by reacting a derivative of 1,4-diaminobenzene with twice molar amount of trimellitic anhydride, Although the reaction conditions are not limited, the reaction usually carried out at temperatures of from 150° C. to 180° C., under an atmospheric pressure or a reduced pressure, for 5 to 10 hours.

The reaction should be conducted in a polar solvent such as dimethylacetamide, dimethylformamide, dimethyl sulfoxide, N-methylformamide, N-methyl-2-pyrrolidone, sulfolane, and N,N,N',N'-tetramethylure.

It is desirable to conduct the reaction in the flow of an inert gas such as nitrogen and argon.

The polyester polymers of the present invention can be prepared by reacting the four raw material components mentioned above. In this case, the reaction is desirably carried out in two stages.

That is, in the first stage, elimination of alphatic acid is carried out by reacting the raw materials for 1 to 2 hours, at a temperature of from 250° C. to 300° C., at atmospheric pressure, and then, in the second stage, transesterification is carried out by reacting for 1 to 5 hours under a reduced pressure at a temperature of from 250° C. to 320° C.

The reaction is preferably carried out in an atmosphere of an inert gas such as argon or the like.

The reaction can be carried out without a catalyst, but a catalyst such as cobalt may be also employed in order to accelerate the polymerization.

The novel polyester polymers obtained according to the present invention due to their excellent mechanical strength and heat resistance are useful for the production of molded materials, and as well have a sufficient strength in the form of filaments.

The novel polyester polymers of the present invention can be made into useful manufactured articles by the use of conventional general methods and general apparatuses. For example, the novel polyester polymers can be made into fiber by the use of general techniques of melt spinning, and can be injection molded by the use of conventional general apparatuses and techniques.

The novel polyester polymers of the present invention may further contain fillers, pigments, glass fibers, asbestos fibers, antioxidants, stabilizers, plasticizers, lubricants, and other additives.

EXAMPLES AND COMPARATIVE EXAMPLES

The present invention will now be described in details with reference to the following Examples that by no means limit the scope of the invention.

EXAMPLE 1

Into a 1-liter flask equipped with a stirrer, reflux condenser, and nitrogen gas inlet were placed 76.8 g (0.4 mol) of trimellitic anhydride, 28.5 g (0.2 mol) of 1,4-diamino-2-chlorobenzene, and 500 ml of dimethylacetamide as solvent, and the mixture was then stirred at room temperature till it became an homogeneous solution while blowing nitrogen gas into the flask. The obtained product was poured into 3 liters of water, and the precipitate was recovered by filtration and then washed with successive water and methanol to obtain 95.2 g of light red crystals.

The obtained product had a melting point of 390° C. and exhibited liquid crystal properties at temperatures ranging from 270° to 390° C.

The results of elementary analysis was as follows.

|  | Anal. Found | Calcd. |
| --- | --- | --- |
| carbon | 58.6% | 58.7% |
| hydrogen | 2.2% | 2.2% |
| oxygen | 26.2% | 26.1% |
| nitrogen | 5.6% | 5.7% |
| chlorine | 7.4% | 7.3% |

By the infrared absorption analysis of the compound, the following absorptions were observed: 1580 cm$^{-1}$ and 1490 cm$^{-1}$ (benzene nucleus), 1650 cm$^{-1}$ (carbonyl radical), 1780–1680 cm$^{-1}$ and 720 cm$^{-1}$ (imido radical). By these results, the compound was determined to have the following structure.

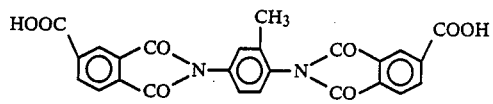

EXAMPLE 2

The procedure of Example 1 was repeated with the exception that 39.0 g (0.2 mol) of 1,4-diamino-2-methylbenzene dihydrochloride was used in place of 1,4-diamino-2-chlorobenzene, and 84.6 g of white crystals were obtained. The melting point of the obtained compound was 410° C. The results of elementary analysis was as follows.

|  | Anal. Found | Calcd. |
| --- | --- | --- |
| carbon | 63.9% | 63.8% |
| hydrogen | 2.9% | 3.0% |
| oxygen | 27.0% | 27.2% |
| nitrogen | 6.2% | 6.0% |

By infrared absorption spectrum analysis of the compound, the following absorptions were observed: 1580 cm$^{-1}$ and 1490 cm$^{-1}$ (benzene nucleus), 1650 cm$^{-1}$ (carbonyl radical), 1780–1680 cm$^{-1}$ and 720 cm$^{-1}$ (imido radical).

By these results, the compound was determined to have the following structure.

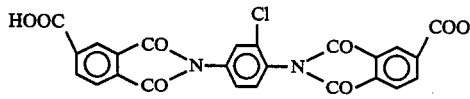

EXAMPLE 3

Into a reaction vessel equipped with a stirrer and argon gas inlet were placed 7.68 g (0.04 mol, in monomer unit), 9.0 g (0.05 mol) of p-acetoxybenzoic acid, 2.60 g (0.01 mol) of 4,4'-diacetoxybiphenyl, and 4.91 g (0.01 mol) of 1,4-bis(4'-carboxyphthalimido)-2-chlorobenzene obtained in Example 1. The mixture was heated to 280° C. in argon stream, and then reacted for 1 hour with stirring. During the reaction, the formed acetic acid was distilled out. The pressure in the reaction vessel was then reduced to 1 mmHg, and reaction was further carried out for 2 hours at 280° C. with stirring. 15.9 g of a copolymer was obtained.

The copolymer had a reduced viscosity [ηsp/c] of 0.65 dl/g as measured in p-chlorophenol at a concentration of 0.2 g/dl at 60° C. By infrared absorption spectrum analysis, the following absorption were observed: 1580 cm$^{-1}$ and 1490 cm$^{-1}$ (benzene nucleus), 1650 cm$^{-1}$ (carbonyl radical), 1240 cm$^{-1}$ (ether bond), 1780–1680 cm$^{-1}$ and 720 cm$^{-1}$ (imido radical).

By these results, the copolymer was determined to comprise the following four types of repeating units.

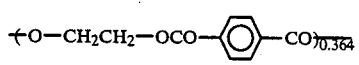 [I]

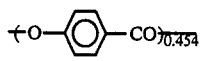 [II]

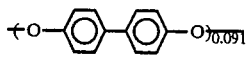 [III]

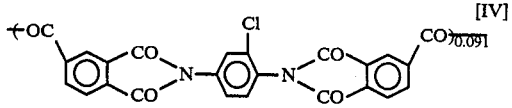 [IV]

Observation with a polarization microscope showed that the polyester polymer exhibits liquid crystal properties at temperatures of not less than 250° C.

The obtained polyester polymer was injection molded, and the load-deflection temperature at a load of 18.5 kg/cm$^2$ was measured according to JIS-K-7207. The heat distortion temperature of the copolymer was 105° C.

Then, the polyester polymer was span from a spinneret of 1 mm in bore diameter at 300° C. to obtain a filament of 30 μm in diameter. The properties of the filament were measured according to JIS-L-1069. The results are shown in Table.

EXAMPLE 4

The procedure of Example 3 was repeated with the exception that the amount of p-acetoxybenzoic acid was changed to 9.9 g (0.055 mol), the amount of 4,4'- diacetoxybiphenyl was changed to 1.30 g (0.005 mol), and the amount of 1,4-bis(4-carboxyphthalimido)-2-chlorobenzene to was changed to 2.46 g (0.005 mol), and 17.2 g of a copolymer was obtained.

The reduced viscosity [ηs/c] of the copolymer was 0.58 dl/g. Further, the copolymer was determined to comprise the following four types of repeating units.

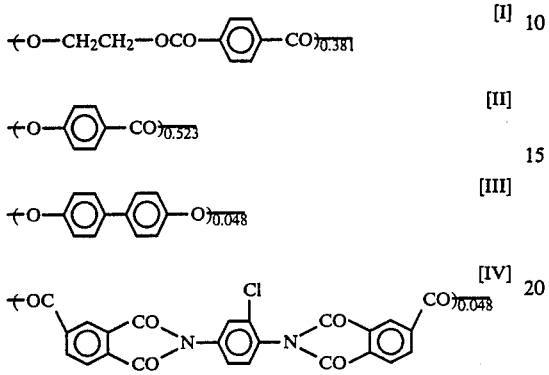

The heat distortion temperature of the copolymer was 85° C.

The properties of the filament made from the polyester polymer by the same way as of Example 3 are shown in Table.

EXAMPLE 5

The procedure of Example 3 was repeated with the exception that the amount of polyethyleneterephthalate was changed to 9.60 g (0.05 mol), the amount of p-acetoxybenzoic acid was changed to 3.60 g (0.02 mol), the amount of 4,4'-diacetoxybiphenyl was changed to 7.80 g (0.03 mol), and the amount of 1,4-bis(4-carboxyphthalimido)-2-chlorobenzene was changed to 14.73 g (0.03 mol), and 22.3 g of a copolymer was obtained.

The reduced viscosity [ηsp/c] of the copolymer was 0.73 dl/g. Further, the copolymer was determined to comprise the following four types of repeating units.

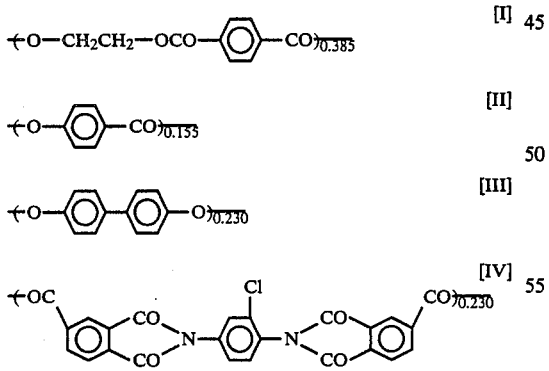

The heat distortion temperature of the copolymer was 110° C.

The properties of the filament made from the polyester polymer by the same way as of Example 3 are shown in Table.

EXAMPLE 6

The procedure of Example 3 was repeated with the exception that 1.94 g (0.01 mol) of p-phenylene diacetate was used in place of 4,4'-diacetoxybiphenyl, and 19.1 g of a copolymer was obtained.

The reduced viscosity [ηsp/c] of the copolymer was 0.63 dl/g. The results of infrared absorption analysis were identical with those of Example 3. Thus, the copolymer was determined to comprise the following four types of repeating units.

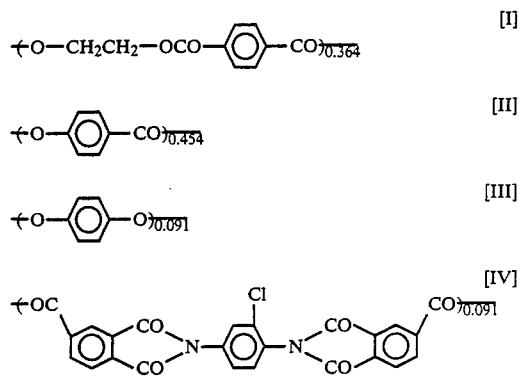

The heat distortion temperature of the copolymer was 95° C.

The properties of the filament made from the polyester polymer by the same way as of Example 3 are shown in Table.

EXAMPLE 7

Into a reaction vessel equipped with a stirrer and argon gas inlet were placed 3.84 g (0.025 mol, in monomer unit) of polyethyleneterephthalate, 12.6 g (0.07 mol) of p-acetoxybenzoic acid, 2.86 g (0.01 mol) of bis(4-acetoxyphenyl)ether, and 4.9 g (0.01 mol) of 1,4-bis(4-carboxyphthalimido)-2-chlorobenzene obtained in Example 1. The mixture was heated to 280° C. in argon gas stream, and then reacted for 1 hour with stirring. During the reaction, formed acetic acid was distilled out. Thereafter, The pressure in the reaction vessel was reduced to 1 mmHg, and the reaction was then further carried out for 6 hours at 30° C. with stirring. Thus, 19 g of a copolymer was obtained.

The copolymer had a reduced viscosity [ηsp/c] of 1.05 dl/g as measured in p-chlorophenol at 60° C. The infrared absorption spectrum of the copolymer was identical with that of Example 3, and the copolymer was determined to comprise the following four types of repeating units.

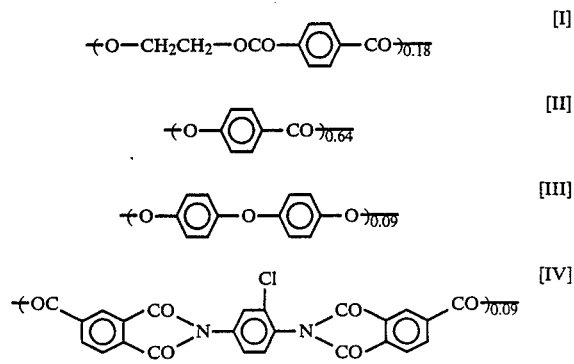

Observation with a polarization microscope showed that the copolymer exhibits liquid crystal properties at temperatures of not less than 250° C. The heat distortion temperature of the copolymer was 135° C.

The properties of the filament obtained by the same way as of Example 3 are shown in Table.

EXAMPLE 8

The procedure of Example 7 was repeated with the exception that 3.02 g (0.01 mol) of bis(4-acetoxyphenyl)sulfide was used in place of bis(4-acetoxyphenyl)ether to obtain a polymer.

The reduced viscosity [ηsp/c] of the copolymer was 1.33 dl/g. Further, the copolymer was determined to comprise the following four types of repeating units.

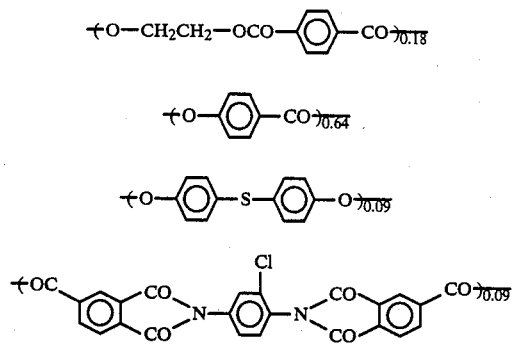

The polyester polymer exhibited liquid crystal properties at temperatures of not less than 280° C. The heat distortion temperature of the copolymer was 125° C. The properties of the filament of 41 μm in diameter made therefrom are shown in Table.

EXAMPLE 9

The procedure of Example 7 was repeated with the exception that 3.12 g (0.01 mol) of 2,2-bis(4-acetoxyphenyl)propane was used in place of bis(4-acetoxyphenyl)ether to obtain a copolymer.

The reduced viscosity [ηsp/c] of the copolymer was 1.20 dl/g. Further, The copolymer was determined to comprise the following four types of repeating units.

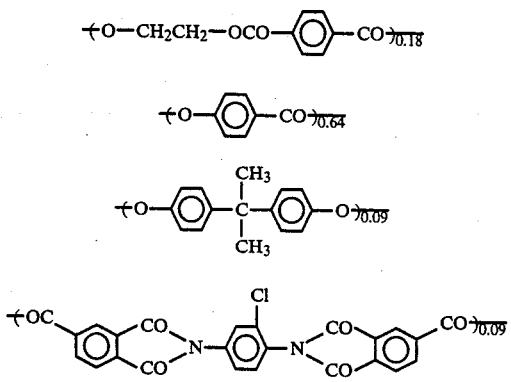

The polyester polymer exhibited liquid crystal properties at temperatures of not less than 230° C. The heat distortion temperature of the copoymer was 140° C. The properties of the filament made therefrom are shown in Table.

EXAMPLE 10

The procedure of Example 7 was repeated with the exception that 3.40 g (0.01 mol) of 2,2-bis(3-methyl-4-acetoxyphenyl)propane was used in place of bis(4-acetoxyphenyl)ether to obtain a copolymer.

The reduced viscosity [ηsp/c] of the copolymer was 1.40 dl/g. The copolymer was determined to comprise the following four types of repeating units.

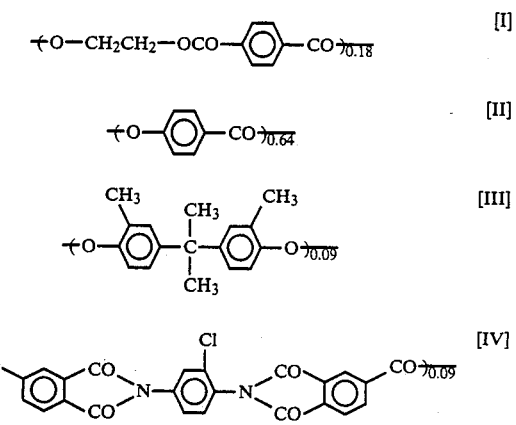

The polyester polymer exhibited liquid crystal properties at temperatures of not less than 250° C. The heat distortion temperature of the copolymer was 130° C. The properties of the filament of 40 μm in diameter made therefrom are shown in Table.

EXAMPLE 11

The procedure of Example 3 was repeated with the exception that 4.70 g (0.01 mol) of 1,4-bis(4'-carboxyphthalimido)-2-methylbenzene obtained in Example 2 was used in place of 1,4-bis(4'-carboxyphthalimido)-2-chlorobenzene to obtain a copolymer.

The reduced viscosity [ηsp/c] of the copolymer was 0.65 dl/g, and the results of infrared absorption spectrum analysis were identical with those of Example 3. Thus, the copolymer was determined to comprise the following four types of repeating units.

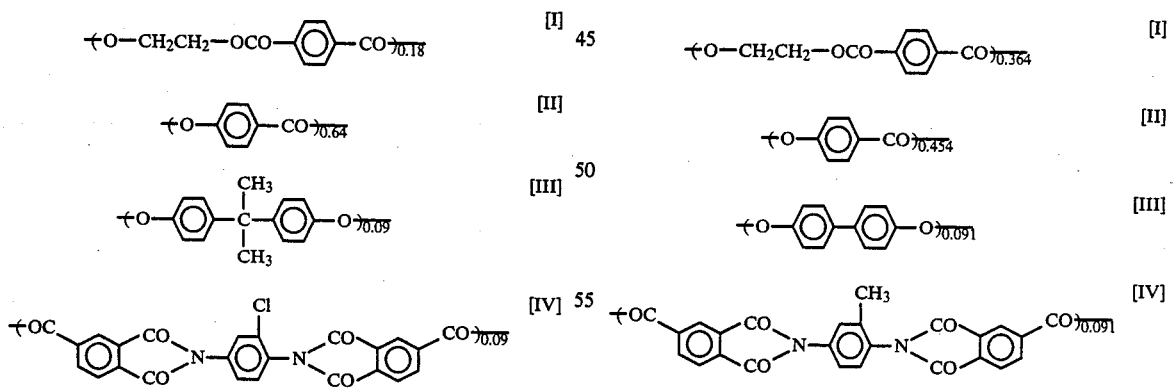

The heat distortion temperature of the copolymer was 98° C. The properties of the filament obtained by the same way as of Example 3 are shown in Table.

EXAMPLE 12

The procedure of Example 3 was repeated with the exception that 12.8 g (0.05 mol) of 4-(4'-acetoxyphenyl)-benzoic acid was used in place of p-acetoxybenzoic acid, and 21.0 g of a copolymer was obtained.

The reduced viscosity [ηsp/c] was 0.35 dl/g. The copolymer was determined to comprise the following four types of repeating units.

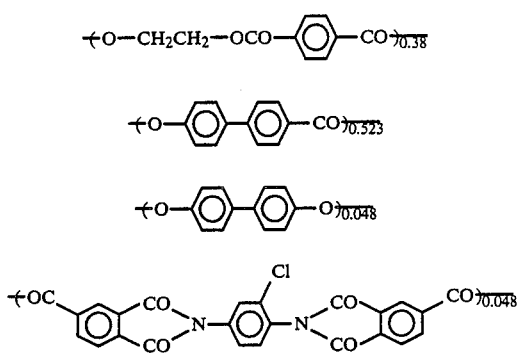

The heat distortion temperature of the copolymer was 120° C. The properties of the filament made from the polyester polymer by the same way as of Example 3 are shown in Table.

COMPARATIVE EXAMPLE 1

The procedure of Example 3 was repeated with the exception that 7.68 g (0.04 mol, in monomer unit) of polyethyleneterephthalate and 10.8 g (0.06 mol) of p-acetoxybenzoic acid were used as raw materials, and 14.1 g of a copolymer was obtained.

The reduced viscosity [ηsp/c] of the copolymer was 0.55 dl/g. The copolymer was determined to comprise the following two types of repeating units.

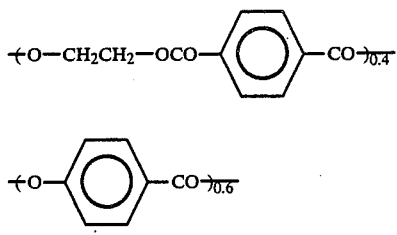

The heat distortion temperature of the copolymer was 67° C. The properties of the filament made from the polyester by the same way as of Example 3 are shown in Table.

COMPARATIVE EXAMPLE 2

The procedure of Example 1 was repeated with the exception that 1,4-bis(4'-carboxyphthalimido)benzene, which is a known diimide-dicarboxylic acid, was used in place of 1,4-bis(4'-carboxyphthalimido)-2-chlorobenzene. However, the diimide-dicarboxylic acid didn't melt at 280° C. and could not form an homogeneous liquid phase with other comonomers. The resulting product was heterogeneous, and had a difficulty in molding since it had no thermal plasticity.

TABLE

| | PROPERTIES OF FILAMENT | | | |
|---|---|---|---|---|
| | DIAMETER OF FILAMENT (μm) | TENSILE STRENGTH (GPa) | TENSILE MODULOUS (GPa) | ELONGATION (%) |
| EXAMPLE 3 | 30 | 0.46 | 45 | 1.3 |
| EXAMPLE 4 | 30 | 0.48 | 35 | 1.6 |
| EXAMPLE 5 | 30 | 0.45 | 43 | 0.5 |
| EXAMPLE 6 | 30 | 0.45 | 34 | 2.0 |
| EXAMPLE 7 | 40 | 0.36 | 30 | 1.5 |
| EXAMPLE 8 | 41 | 0.30 | 28.5 | 1.6 |
| EXAMPLE 9 | 40 | 0.28 | 25.6 | 1.4 |
| EXAMPLE 10 | 40 | 0.30 | 27 | 2.0 |
| EXAMPLE 11 | 35 | 0.25 | 32 | 1.8 |
| EXAMPLE 12 | 40 | 0.30 | 35 | 0.8 |
| COMPARATIVE EXAMPLE 1 | 30 | 0.19 | 26 | 1.8 |

What is claimed is:

1. A polyester polymer consisting essentially of repeating units having the formula

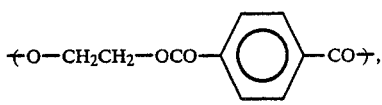

repeating units having the formula

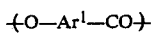

repeating units having the formula

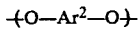

and repeating units having the formula

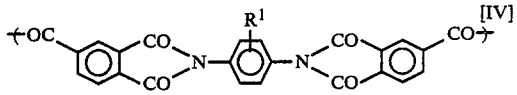

wherein
Ar$^1$ is selected from

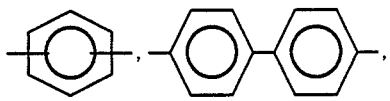

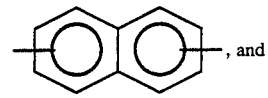, and

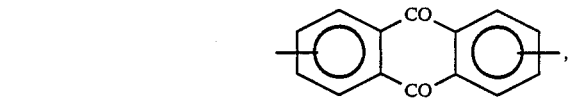

Ar$^2$ is selected from

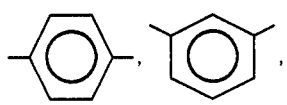

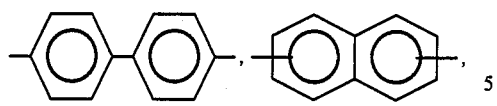

halogen substituted radicals of these radicals, and

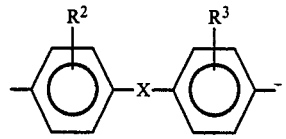

wherein
X is selected from —O—, —S—, —SO$_2$—, —CO—, —O(CH$_2$)$_n$O—(CH$_2$)$_n$—, and

wherein each n independently represents a number having a value of from 1 to 10, and each R$^4$ is independently selected from alkyl radicals of 1 to 5 carbon atoms, and R$^2$ and R$^3$ are independently selected from hydrogen atom, halogen radicals, alkyl radicals of 1 to 5 carbon atoms, and phenyl radical, and R$^2$ and R$^3$ may be identical or different from each other, and R$^1$ is selected from halogen radicals and alkyl radicals of 1 to 5 carbon atoms, and wherein the polyester polymer has a reduced viscosity [$\eta$sp/c] of at least 0.2 dl/g as measured in p-chlorophenol at a concentration of 0.2 g/dl at 60° C.

2. A polyester polymer as defined in claim 1 wherein Ar$^1$ is

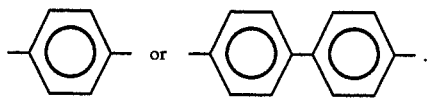

3. A polyester polymer as defined in claim 1 wherein Ar$^2$ is

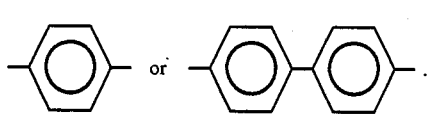

4. A polyester polymer as defined in claim 1 wherein Ar$^2$ is selected from

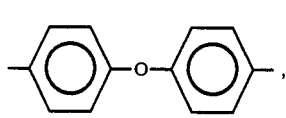

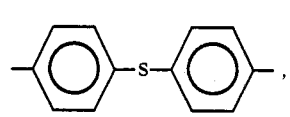

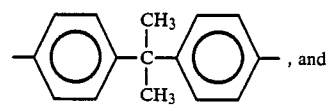

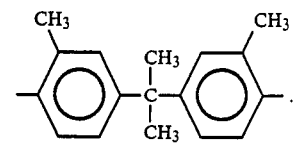

5. A polyester polymer as defined in claim 1 wherein the mole fraction of the repeating units having the formula [I] is from 5 to 50%, the mole fraction of the repeating units having the formula [II] is from 5 to 70%, the mole fraction of the repeating units having the formula [III] is from 5 to 50%, and the mole fraction of the repeating units having the formula [IV] is from 5 to 50%.

6. A process for preparing a polyester polymer comprising reaction [A] a polyethyleneterephthalate, [B] an acyloxy-aromatic carboxylic acid having the formula R$^5$—CO—O—Ar$^1$—COOH wherein
R$^5$ is selected form alkyl radicals of 1 to 3 carbon atoms and
Ar$^1$ is selected from

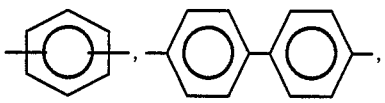

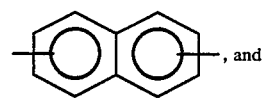

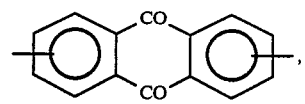

[C] an ester having the formula

RCOO—Ar$^2$—OCOR wherein
each R is independently selected from alkyl radicals of 1 to 20 carbon atoms and
Ar$^2$ is selected from

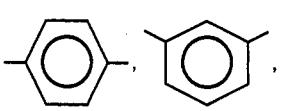

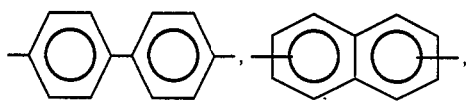

halogen substituted radicals of these radicals, and

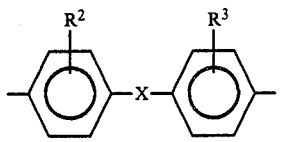

wherein

X is selected from —O—, —S—, —SO₂—, —CO—, —O(CH₂)ₙO—, -(CH₂)ₙ, and

wherein each n independently represents a number having a value of from 1 to 10 and each $R^4$ is independently selected from alkyl radicals of 1 to 5 carbon atoms, and $R^2$ and $R^3$ are independently selected from hydrogen atom, halogen radicals, alkyl radicals of 1 to 5 carbon atoms, and $R^2$ and $R^3$ may be identical or different from each other, and [D] a diimide-dicarboxylic acid having the formula

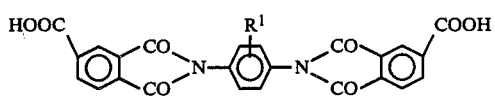

wherein $R^1$ is selected from hydrogen atom, halogen radicals, and alkyl radicals of 1 to 5 carbon atoms.

7. A process for preparing a polyester polymer as defined in claim 6 wherein the polyethyleneterephthalate [A] has a reduced viscosity [ηsp/c] of from 0.1 to 1.0 dl/g as measured in p-chlorophenol at a concentration of 0.2 g/dl at 60° C.

8. A process for preparing a polyester polymer as defined in claim 6 wherein the acyloxy-aromatic carboxylic acid [B] has the formula

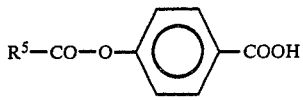

wherein $R^5$ is as defined above.

9. A process for preparing a polyester polymer as defined in claim 8 wherein the acyloxy-aromatic carboxylic acid [B] is p-acetoxybenzoic acid or 4-(4'-acetoxyphenyl)benzoic acid.

10. A process for preparing a polyester polymer as defined in claim 6 wherein the ester [C] is 4,4'-diacetoxybiphenyl or p-phenylene diacetate.

11. A process for preparing a polyester polymer as defined in claim 6 wherein the ester [C] is selected from bis(4-acetoxyphenyl)ether, bis(4-acetoxyphenyl)sulfide, 2,2-bis(4-acetoxyphenyl)propane, and 2,2-bis(3-methyl-4-acetoxyphenyl)propane.

12. A process for preparing a polyester polymer as defined in claim 6 wherein the diimide-dicarboxylic acid [D] is 1,4-bis(4'-carboxyphthalimido)-2-chlorobenzene or 1,4-bis(4'-carboxyphthalimido)-2-methylbenzene.

13. A process for preparing a polyester polymer as defined in claim 6 wherein, in first stage, [A] a polyethyleneterephthalate, [B] an acyloxy-aromatic carboxylic acid, [C] an ester, and [D] a diimidedicarboxylic acid are reacted for 1 to 2 hours at atmospheric pressure at a temperature of from 250° C. to 300° C., and subsequently, in second stage, reacted for 1 to 5 hours under a reduced pressure at a temperature of from 250° C. 320° C.

14. A diimide-dicarboxylic acid having the formula

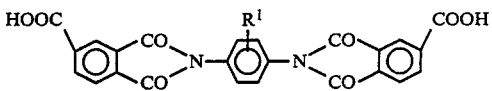

wherein $R^1$ is selected from hydrogen atom, halogen radicals, and alkyl radicals of 1 to 5 carbon atoms.

15. 1,4-Bis(4'-carboxyphthalimido)-2-chlorobenzene.
16. 1,4-Bis(4'-carboxyphthalimido)-2-methylbenzene.

* * * * *

UNITED STATES PATENT AND TRADEMARK OFFICE
CERTIFICATE OF CORRECTION

PATENT NO. : 4,749,775
DATED : June 7, 1988
INVENTOR(S) : T. TAKEYA, et al

It is certified that error appears in the above-identified patent and that said Letters Patent is hereby corrected as shown below:

Title page, left-hand column, please add the following after "[22] Filed: Jul. 7, 1987"

--[30]     Foreign Application Priority Data
  Jul 7, 1986 [JP]   Japan....................61-157963--

Signed and Sealed this

Thirteenth Day of December, 1988

Attest:

DONALD J. QUIGG

*Attesting Officer*     *Commissioner of Patents and Trademarks*